(12) United States Patent
Yen et al.

(10) Patent No.: US 10,422,705 B2
(45) Date of Patent: Sep. 24, 2019

(54) APPARATUS AND METHOD FOR MEASURING BODY TEMPERATURE OF A HUMAN BODY

(71) Applicants: Nelson Yen, Brea, CA (US); Ding Yuan Yen, Brea, CA (US)

(72) Inventors: Ding Yuan Yen, Kowloon (HK); Hsaio Wei Fang, New Taipei (TW); Te Min Lai, Taichung (TW)

(*) Notice: Subject to any disclaimer, the term of this patent is extended or adjusted under 35 U.S.C. 154(b) by 126 days.

(21) Appl. No.: 15/438,127

(22) Filed: Feb. 21, 2017

(65) Prior Publication Data

US 2017/0248478 A1  Aug. 31, 2017

(30) Foreign Application Priority Data

Feb. 26, 2016 (CN) .......................... 2016 1 0106457

(51) Int. Cl.
G01K 3/06 (2006.01)
G01K 13/00 (2006.01)
(Continued)

(52) U.S. Cl.
CPC .......... *G01K 13/004* (2013.01); *A61B 5/0082* (2013.01); *A61B 5/01* (2013.01);
(Continued)

(58) Field of Classification Search
CPC .................................................. G01K 13/004
See application file for complete search history.

(56) References Cited

U.S. PATENT DOCUMENTS 4,150,573 A * 4/1979 Iinuma .................. G01K 7/245
324/707
7,340,293 B2 * 3/2008 McQuilkin ............ A61B 5/015
374/121
(Continued)

FOREIGN PATENT DOCUMENTS

CN 204192587 U * 3/2015

OTHER PUBLICATIONS

Ludwig, N., D. Formenti, M. Gargano, and G. Alberti. "Skin Temperature Evaluation by Infrared Thermography: Comparison of Image Analysis Methods." Infrared Physics & Technology 62 (2014): 1-6. doi:10.1016/j.infrared.2013.09.011.*
(Continued)

*Primary Examiner* — Clayton E. LaBalle
*Assistant Examiner* — Leon W Rhodes, Jr.
(74) *Attorney, Agent, or Firm* — Sanford Astor

(57) ABSTRACT

The invention relates to an apparatus for measuring the human body temperature. It comprises of an infrared temperature sensor for performing temperature sampling on a plurality M×N of sampling points, M≥3, N≥3. The temperatures of the sampling points with temperatures within the effective temperature range of the human body are averaged to obtain the body temperature of the human body. By collecting the temperatures of a plurality of sampling points of the measured object, the invention effectively avoids the errors that measurement of single point may produce (as may be caused by factors such as the environment); by screening for temperatures within the effective temperature range of the human body, the invention effectively avoids errors or interference produced by factors such as clothing or the environment. The improved accuracy and real-time measurement of body temperature bring convenience to people's lives.

4 Claims, 3 Drawing Sheets

(51) Int. Cl.
*A61B 5/01* (2006.01)
*A61B 5/00* (2006.01)

(52) U.S. Cl.
CPC ............... *G01K 3/06* (2013.01); *A61B 5/015* (2013.01); *A61B 5/7235* (2013.01); *A61B 2562/0271* (2013.01)

(56) References Cited

U.S. PATENT DOCUMENTS

| | | | | |
|---|---|---|---|---|
| 8,517,603 | B2* | 8/2013 | Fraden | G01J 5/0003 |
| | | | | 374/121 |
| 9,204,062 | B2* | 12/2015 | Bergstrom | H04N 5/2258 |
| 2007/0153871 | A1* | 7/2007 | Fraden | A61B 5/015 |
| | | | | 374/121 |
| 2013/0083823 | A1* | 4/2013 | Harr | G01J 5/026 |
| | | | | 374/121 |
| 2013/0230074 | A1* | 9/2013 | Shin | G01J 5/0025 |
| | | | | 374/129 |
| 2016/0192620 | A1* | 7/2016 | Hu | A01K 5/0114 |
| | | | | 119/51.02 |

OTHER PUBLICATIONS

Allain, "Trying Out the iPhone Infrared Camera: The FLIR One", retrieved from https://www.wired.com/2014/08/a-review-of-the-iphone-infrared-camera-the-flir-one/ (Year: 2014).*

Translation of First Office Action in Chinese application 201610106457, dated Feb. 2, 2018 (Year: 2018).*

Translation of Second Office Action in Chinese application 201610106457, dated Sep. 14, 2018 (Year: 2018).*

* cited by examiner

| 1 | 2 | 3 | 4 | 5 | 6 | 7 | 8 | 9 |
|---|---|---|---|---|---|---|---|---|
| 10 | 11 | 12 | | | 16 | 17 | 18 | |
| 19 | 20 | 21 | | | | 26 | 27 | |
| 28 | 29 | | | | | 35 | 36 | |
| 37 | 38 | | | 43 | 44 | 45 | | |
| 46 | 47 | 48 | | 52 | 53 | 54 | | |
| 55 | 56 | | | | 62 | 63 | | |
| 64 | 65 | | | | 71 | 72 | | |
| 73 | | | | | | 81 | | |
| | 84 | | 88 | | | | | |
| 91 | 93 | | 97 | | 99 | | | |
| 100 | 101 | 102 | | 106 | 107 | 108 | | |
| 109 | 110 | 111 | | 115 | 116 | 117 | | |
| 118 | 119 | 120 | | 124 | 125 | 126 | | |
| 127 | 128 | | | 133 | 134 | 135 | | |
| 136 | 137 | | | | 143 | 144 | | |

| 1 | 2 | 3 | 4 |
|---|---|---|---|
| 5 | 6 | 7 | 8 |
| 9 | 10 | 11 | 12 |
| 13 | 14 | 15 | 16 |
| 17 | 18 | 19 | 20 |
| 21 | 22 | 23 | 24 |
| 25 | 26 | 27 | 28 |
| 29 | 30 | 31 | 32 |
| 33 | 34 | 35 | 36 |
| 37 | 38 | 39 | 40 |
| 41 | 42 | 43 | 44 |
| 45 | 46 | 47 | 48 |
| 49 | 50 | 51 | 52 |
| 53 | 54 | 55 | 56 |
| 57 | 58 | 59 | 60 |
| 61 | 62 | 63 | 64 |

*FIG. 2*

The infrared temperature sensor measures the temperatures of the 64 sampling points

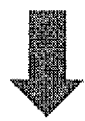

The 64 sampled points are analyzed, and those points which have temperatures 35 C – 42 C (human body temperature range) are retained

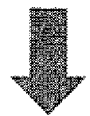

The temperatures of sampling points which belong to the effective temperature range are averaged, and the averaged temperature obtained is the human body temperature

*FIG. 3*

APPARATUS AND METHOD FOR MEASURING BODY TEMPERATURE OF A HUMAN BODY

CROSS-REFERENCE TO RELATED APPLICATIONS

This application claims priority of Chinese Patent Application No. 201610106457.X, filed on Feb. 26, 2016, the entire contents of which are hereby incorporated herein by reference.

TECHNICAL FIELD

The present invention relates to a method for measuring the body temperature of a human body, and more particularly, to an apparatus and method for measuring body temperature of a human body based on a multi-point infrared temperature sensor.

BACKGROUND

In recent years, with improvements in infrared temperature measurement technology, non-contact infrared thermometers have experienced rapid development, better performance, and continuous improvement. Compared with the contact temperature measurement method, infrared temperature has benefits such as fast response time, is non-contact, may be safer, and others. Infrared detection is a kind of on-line monitoring type high-tech detection technology, which integrates photoelectric imaging technology, computer technology and image processing technology. It receives the infrared ray (infrared radiation) from the object and displays its thermal image on the screen with accuracy and speed.

With the progress of the times, people's temperature and other parameters of the measurement of life have new requirements not satisfied with the traditional thermometer-based measurement. Infrared temperature measurement based on infrared detection is a new fast, convenient and safe temperature measurement method that can achieve not only non-contact temperature measurement, but also real-time, rapid access to body temperature data. However, the existing infrared temperature measurement device using a single point of measurement, is susceptible to ambient temperature interference, and the error is large. Achieving accurate temperature measurement with infrared technology is a technical problem to be solved urgently.

SUMMARY

In order to solve the technical problem that the body temperature can not be accurately measured in the prior art, the invention provides an apparatus and method for measuring the body temperature of the human body based on the infrared temperature sensor. This is done by including a high precision infrared temperature sensor in the camera, and eliminating the sampling temperature which is obviously not within the human body temperature range. The remaining sampled effective temperatures are averaged to obtain more accurate temperature data, which greatly reduces the interference of the ambient temperature and realizes real-time, fast, non-contact body temperature measurement.

The technical proposal of the present invention for solving the above technical problems is as follows:

An apparatus for measuring the human body temperature. It comprises of an infrared temperature sensor for performing temperature sampling on a plurality M×N of sampling points, M≥3, N≥3. The temperatures of the sampling points with temperatures within the effective temperature range of the human body are averaged to obtain the body temperature of the human body.

Further, the effective body temperature interval is 35° C. to 42° C.

In addition, the invention also provides a method for measuring body temperature of a human body, comprising the following steps:
1) the use of infrared temperature sensor to measure the temperature of a sampling point;
2) determine whether the temperature of each sampling point falls into the effective human body temperature range;
3) calculating the average value of the temperature falling into the effective body temperature range, namely, the human body temperature.

Further, the effective body temperature range is 35° C. to 42° C.

Compared with the prior art, the invention effectively avoids the errors that measurement of single point may produce (as may be caused by factors such as the environment); by screening for temperatures within the effective temperature range of the human body, the invention effectively avoids errors or interference produced by factors such as clothing or the environment. The improved accuracy and real-time measurement of body temperature bring convenience to people's lives.

BRIEF DESCRIPTION OF THE DRAWINGS

FIG. 2 is a schematic representation of the temperature sampling of the infrared temperature sensor of the present invention;

FIG. 3 is a flow chart of the body temperature measurement of the present invention.

DETAILED DESCRIPTION

Figure 1:
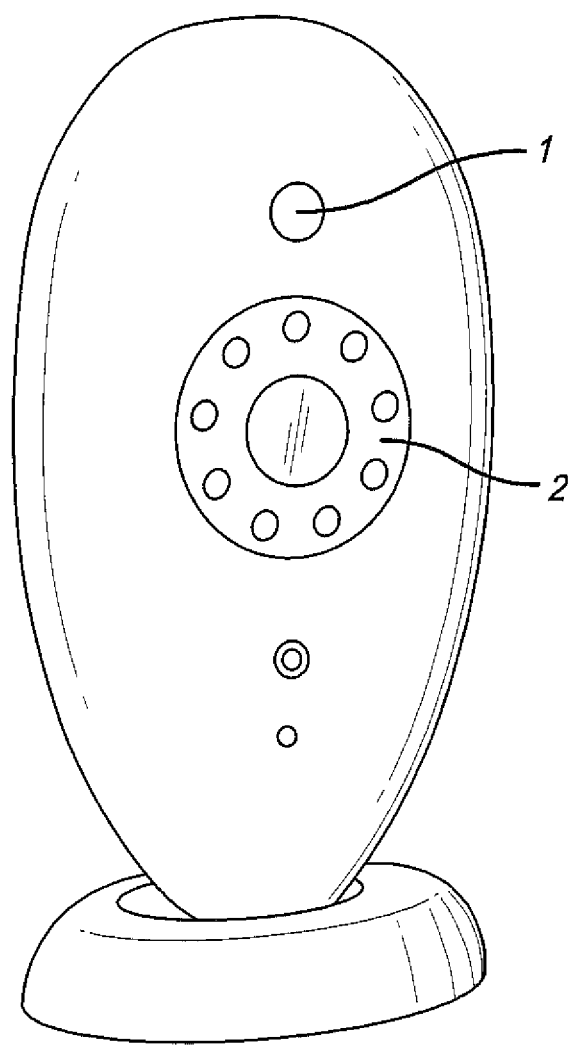
FIG. 1 is a schematic view of a body temperature measuring apparatus of the present invention.

For the purpose of describing the principles and the technical solutions of the present invention, the following description will be made in detail with reference to the accompanying drawings. The examples are illustrative only and are not intended to limit the scope of the invention.

Normal body temperature is generally 36.1° C.~37° C., lower than the oral temperature by about 0.2° C.~0.4° C., according to the level of fever (oral temperature), can be divided into: low heat: 37.4° C.~38° C.; 39° C. to 41° C.; ultra-high heat: 41° C. or higher; and in the present invention, the effective temperature range of the human body is set to 35° C. to 42° C., and points are only considered when the collected temperature falls within the above-mentioned effective temperature range. Otherwise, it means that the corresponding sampling points do not belong to the human body area or the human body area is blocked by other objects, resulting in abnormal temperature. By eliminating the above abnormal temperature, the average temperature of the sample obtained can produce more accurate body temperature data, avoiding the errors of single point measurement due to the impact of environmental interference. The above is an explanation of the principle of the present invention, and the following description will be given by way of example.

FIG. 1 is a schematic diagram of the device for measuring body temperature of the present invention, and a high-precision infrared temperature sensor 1 is arranged above the camera 2. The infrared temperature sensor can collect the temperature of 64 sampling points at the same time, the effective temperature collection distance is more than 1.5 meters. The points are distributed in a matrix, as shown in FIG. 2, 64 sampling points are distributed in the whole imaging area. When the human body is detected in the camera shooting area, the infrared temperature sensor is triggered to carry out the temperature sampling, and the temperature corresponding to the 64 sampling points is obtained. Only some of the sampling points fall within the effective region of the human body. FIG. 3 shows a flow chart of the present invention for measuring body temperature of a human body comprising the steps of:

S1, the infrared temperature sensor measures the temperatures of the 64 sampling points.

S2, the 64 temperature data collected is analyzed. Because some of the sampling points are not covered by the human body, or because of object occlusion and other reasons, some of the sampling points of the temperature significantly deviate from the human body temperature range. In calculating the body temperature, abnormal points are removed from the sampling points. If the temperature of the sampling point is not within the effective temperature range of the human body, it is considered that the temperature is not the effective temperature and is not taken into account in the calculation; if the sampling point has temperature 35° C.~42° C., then it belongs to the effective temperature.

S3, the temperatures of sampling points which belong to the effective temperature range are averaged, and the average temperature obtained is the measured body temperature.

The measured temperature data will be uploaded to the local cloud server in real time. Therefore, no matter where the user is, the user can simply open the browser to the specified page or login account through APP to view real-time camera image and body temperature data, remote body temperature measurement, and monitoring. Preferably, the invention further comprises a face recognition unit which records the historical temperature data of each measured object and when it is found that the body temperature measured by the same subject has a greater difference than the body temperature measured recently by the history, it will note that there may be physical anomalies and will be timely to alert the user about the noted temperature difference.

The foregoing description is only a few examples of the present invention and is not intended to be limiting of the present invention. Any modifications, equivalent substitutions, improvements and the like within the spirit and principles of the invention are intended to be embraced by the present invention Protection range.

What is claimed is:

1. An apparatus for measuring human body temperature, comprising:
   a camera and an infrared temperature sensor arranged within a single unit;
   wherein the infrared temperature sensor has an effective temperature collection distance of 1.5 meters or more and collects temperature information at each of 64 sampling points distributed as a rectangular matrix within the imaging area of the camera;
   the apparatus being configured to calculate a measured human body temperature from the temperature information of sampling points which have temperature information that falls within an effective human body temperature range, and
   the apparatus being configured to transmit a camera image and the measured human body temperature to a remote device in real-time.

2. The apparatus for measuring human body temperature of claim 1, wherein the apparatus is configured to use a temperature range of 35° C. to 42° C. as the effective human body temperature range.

3. A method for measuring the body temperature of a human being, comprising:
   providing a camera and an infrared temperature sensor within a single unit, the infrared temperature sensor having 64 sampling points distributed as a rectangular matrix in the camera imaging area and an effective temperature collection distance of 1.5 meters or more;
   collecting, using the infrared temperature sensor, temperature information at each of 64 sampling points distributed as a rectangular matrix;
   determining whether the temperature information of each sampling point falls into an effective human body temperature range,
   determining a measured human body temperature using only the temperature information from sampling points which fall within the effective human body temperature range, and
   transmitting a camera image and the measured human body temperature to a remote device in real-time.

4. The method of measuring the body temperature of claim 3, wherein a temperature range of 35° C. to 42° C. is used as the effective human body temperature range.

* * * * *